United States Patent [19]
Klein

[11] 3,950,398
[45] Apr. 13, 1976

[54] METHACRYLIC ACID ADDITION SALT OF 2-MONO(LOWER)ALKYL AMINO ETHYL METHACRYLATE

[75] Inventor: Max Klein, New Shrewsbury, N.J.

[73] Assignee: Normac, Inc., New Shrewsbury, N.J.

[22] Filed: Nov. 5, 1973

[21] Appl. No.: 413,043

Related U.S. Application Data

[63] Continuation-in-part of Ser. No. 15,935, March 2, 1970, abandoned, which is a continuation-in-part of Ser. No. 488,756, Sept. 20, 1965, abandoned.

[52] U.S. Cl.............. 260/486 R; 106/14; 252/79 R; 260/42.52; 260/80.73; 260/86.1 N; 260/89.5 N; 428/458
[51] Int. Cl.² ........................................ C07C 69/54
[58] Field of Search .............................. 260/486 R

[56] References Cited
UNITED STATES PATENTS

| | | | |
|---|---|---|---|
| 2,104,796 | 1/1938 | Dietrich | 260/486 |
| 2,138,762 | 11/1938 | Harmon | 260/486 |
| 3,099,636 | 7/1963 | Skiles | 260/486 |
| 3,239,496 | 3/1966 | Jursich | 260/486 |
| 3,336,358 | 8/1967 | McFadden | 260/486 |

*Primary Examiner*—Lorraine A. Weinberger
*Assistant Examiner*—Paul J. Killos

[57] ABSTRACT

Water-soluble, polymerizable, acid addition salts of methacrylic acid and 2-mono-(lower)alkylanimoethyl methacrylate whose lower alkyl group is straight or branched chain or cyclic and has up to about 6 carbon atoms, said addition salt includes its methacrylic acid and methacrylate components in the ratio of from about one mole to about 1.5 moles of one of them per mole of the other.

15 Claims, No Drawings

METHACRYLIC ACID ADDITION SALT OF 2-MONO(LOWER)ALKYL AMINO ETHYL METHACRYLATE

The application is a continuation-in-part application of my copending application Ser. No. 15,935 filed Mar. 2, 1970 now abandoned which in turn is a continuation-in-part of my then copending with it application Ser. No. 488,756 filed Sept. 20, 1965 and now abandoned.

This invention is that of certain solid, water-soluble, polymerizable, acid addition salt products. Each such product is an acid addition salt of (a) methacrylic acid and (b) a 2-mono-(lower)alkylaminoethyl methacrylate whose lower alkyl group is straight or branched chain or cyclic and has up to about 6 carbons; which addition salt includes its methacrylic acid and methacrylate components in the ratio of from about one mole to about 1.5 moles of one of them per mole of the other.

The 2-mono-(lower)alkylaminoethyl methacrylate sometimes hereinbelow briefly is called the "secondary-aminoethyl methacrylate" or at times more briefly simply the "secondary-aminoethyl ester".

More specifically these polymerizable water-soluble solid acid addition salt products as solid compositions comprise the acid addition salt of equimolar parts of methacrylic acid and any aforesaid methacrylate, which addition salt as such solid product contains from none to about 50% molar excess of either the methacrylic acid or said mono-alkylaminoethyl methacrylate component.

An important subgenus of these solid compositions of the invention is the acid addition salt of substantially stoichiometrically equivalent or equimolar quantities of its methacrylic acid and mono-alkylaminoethyl methacrylate components. This type of embodiment of the acid addition salts of the invention briefly is called "the equimolar acid addition salts" of methacrylic acid and the 2-mono-(lower)alkylaminoethyl methacrylate, or singly may be called "an equimolar acid addition salt" of this acid and the particular secondary-aminoethyl methacrylate component.

The expression "component" used herein in referring to a part of an acid addition salt of this invention means that part of the acid addition salt present in it from the respective one of the starting reactants, namely, the methacrylic acid or the specific secondary-aminoethyl ester, from which the particular acid addition salt was made.

These equimolar acid addition salts are useful, for example, as additives to provide the possibility of solution co-polymerization of some polymerizable monomers, such as styrene and acrylonitrile, which when sought to be co-polymerized in solution otherwise are prone to yield not only undesirably low viscosity polymer solutions in the solvents used but also weak and brittle polymer films cast from such solutions. Inclusion of these equimolar addition salts as such additives serves to enhance not only the solution co-polymerization procedure but also the resulting characteristics of the solution of the end product polymer in the solvent used and of the films obtainable from such solutions.

The equimolar acid addition salts further are polymerizable individually in an aqueous system to yield useful aqueous solutions of the resulting homopolymer. They also are polymerizable in low boiling solvents such as an aliphatic hydrocarbon solvent as hexane, butane and especially pentane, for example, at elevated temperature above its boiling point and so also under pressure to yield a water-soluble polymer which precipitates in easily separable light weight finely divided solid state. This polymer manifests interesting polyampholytic properties.

Still further these equimolar acid addition salts can be combined with some polymers, to give final polymeric products of improved and/or advantageously modified properties.

Another subgenus of the acid addition salts of the invention is that of those solid acid addition salts obtained from admixing methacrylic acid and the 2-mono-(lower)alkylaminoethyl methacrylate in other than equimolar proportions, that is to say, in unequal molar proportions, with an excess of either one of them over the other even up to as much as about 50 mole percent and possibly more. This type of the solid salts of this invention conveniently are called briefly the "unequal-molar acid addition salts".

Accordingly, such unequal-molar acid addition salt having an excess of methacrylic acid conveniently briefly is called the "excess-acid unequal-molar acid addition salt". Alternatively, the unequal-molar salt having an excess of the 2-mono-(lower)alkylaminoethyl methacrylate component similarly conveniently is called briefly the "excess-ester unequal-molar acid addition salt". In either case, each of these types of unequal-molar acid addition salts is a water-soluble, waxy-appearing yet readily frangible, uniform-looking solid.

Each of the unequal-molar acid addition salts readily is broken down easily into smaller pieces, by agitating it, often for as little as a few minutes, with a stirring rod, spatula, paddle or in a ribbon blender, depending on the batch size, and with only shortly continued such agitation to smaller granules and still with retained solid state. Each of the two types of these unequal-molar acid addition salts is a polymerizable similarly to the equimolar type, but to yield a water-insoluble polymeric product. Each of these types of unequal-molar acid addition salts also is polymerizable in an aqueous system to provide useful aqueous solutions of the resulting homopolymers.

An initial method of making the equimolar acid addition salts of this invention involves mixing together rapidly a weighed quantity of the methacrylic acid with the stoichiometric equivalent or equimolar quantity of the selected secondary-aminoethyl methacrylate, and quickly pouring their uniform mixture while still liquid into a flat crystallization tray, so that the mixing and pouring into the tray is completed in a total of about ten seconds when the mix while still hot from the evolved heat of the complete neutralization begins to cool down and solidifies into a tough, opaque solid mass.

This resulting cooled opaque and tough solid mass requires heavy-striking crushing blows to break it down into smaller pieces, in contrast to the ready frangibility of the solid unequal-molar acid addition salts thereof.

Alternatively, the equimolar acid addition salts can be made by feeding the methacrylic acid and the secondary-aminoethyl methacrylate in separate streams into a continuous mixer with rapidly rotating stirrers and an outlet directed to a dished continuous crystallization belt for their hot uniform mix to be run onto the belt before the mix has cooled down to solidification temperature (within about ten seconds of their mixing). This requires available but costly control equipment and also yields the same tough finished product requiring heavy blow crushing to disintegrate it.

On the other hand, any of the two types of unequal-molar acid addition salts of the invention is prepared without any such need for rapid handling and completion within a matter of about ten seconds. Instead for the unequal-molar acid addition salt the mixing and pouring off steps can be carried out within as long as about an hour before solidification of the resulting acid addition salt can occur.

Thus, to prepare either of the two types of unequal-molar acid addition salts, the respective amounts of methacrylic acid and of the secondary-aminoethyl methacrylate required to provide the desired molar percent excess of whichever of them is to be in excess, are fed in any convenient way and at any convenient rate into a mixing vessel or tank equipped with a suitable agitator, even a high torque low speed agitator, and running it at a suitably effective speed.

There is no need to adjust the feeding speed of either of the reactants to that of the other for preparing any of these unequal-molar acid addition salts. That is so because any solid acid addition salt which may form while the separate amounts of these reactants is being fed into the mixing tank readily is broken down during the agitation at worst into only a temporary partial slurry state and any such mixture then remains liquid until the entire required amount of both reactants has been added.

Continuing the agitation provides a hot uniformly liquid reaction batch which then can be transferred to any suitable receptacle or container. As the temperature of the liquid falls and it reaches its solidification point, the liquid reaction product solidifies entirely into a readily frangible solid unequal-molar acid addition salt such as is described further above.

As a further part of the invention it was found that its two types of unequal-molar acid addition salts are useful for preparing the equimolar acid addition salts of the invention by a very greatly simplified and considerably less costly procedure which at the same time makes the equimolar acid addition salt available in very finely divided particle size, possibly in the micron range, without any need for crushing and grinding.

Thus, also part of the invention is the method of producing the equimolar acid addition salts of the invention by preparing (a) an excess-acid unequal-molar acid addition salt using up to about 50 mole percent excess methacrylic acid, and preferably with at least about 15 mole percent excess of it; (b) preparing a corresponding excess-water unequal-molar acid addition salt using the same mole percent excess of the secondary-aminoethyl ester as that of the excess of the acid used to prepare the excess-acid unequal-molar acid addition salt, (c) physically breaking down each of these two unequal-molar acid addition salts, either alone or admixed, by agitation as further above described, and (d) if thus physically breaking them down separately, then mixing the smaller pieces of them, and continuing the mixing until all of the agitated mixture of both of these unequal-molar addition salts is converted to very finely divided particles of the resulting equimolar acid addition salt. Then, as may be needed, the finely divided end product addition salt can be allowed to cool to ambient temperature from that which it acquired from heat evolved after mixing together the two different unequal-molar acid addition salts.

The aqueous solutions, even at the low concentrations of a few, or even one, percent of the equimolar acid addition salts of the invention, as well as of each of the two types of unequal-molar addition salts, used alone or jointly, withstand decomposition at elevated temperatures. In addition, such aqueous solutions show significant depression of the freezing point of water, thereby indicating their utility as anti-freeze preparations useful in cooling systems of internal combustion engines as well as in other circulating cooling systems such as the external showers over the exposed pipe condensers of ammonia and similar refrigeration systems.

The invention is illustrated by, but not restricted to, the following examples:

EXAMPLE 1

Equimolar acid addition salt of methacrylic acid and tertiary-butylaminoethyl methacrylate:

185.3 grams (1 mole) of (mono)tertiary-butylaminoethyl methacrylate and 86.5 grams (1 mole) of glacial methacrylic acid separately are poured simultaneously into an aluminum vessel with agitation and at a rate to complete their addition at about the same time. An immediate exothermic reaction occurred at the end of about ten seconds or so with complete conversion of the reaction mixture then to a white, tough, opaque solid mass. During the addition of the reactants, reaction between their vapors produced a light formation of long sharp needle-like crystals of the equimolar acid addition salt on the walls of the vessel, but during the agitation these were washed down in the initially liquid reaction mixture when addition of both of the reactants was completed and so became a uniform part of the final solid mass of end product equimolar acid addition salt.

This example was repeated. After admixture of the reactants and while the uniform reaction mixture still was liquid and before it could solidify, the entire contents of the reaction vessel was poured into a flat crystallization tray. Its temperature then was about 94° C. Solidification started within a few seconds and at a temperature of about 90° C. it soon was complete.

The solid mass of end product was removed from the tray, broken into chunks and ground to a fine white powder. The latter did not appear to be hygroscopic and did not change in color or appearance even after long extended exposure to the ambient atmosphere. This equimolar acid addition salt readily dissolved in cold water in any concentrations even up to 50 percent (the highest prepared), in methanol, acetone, and methyl ethyl ketone, at ambient temperature and above, and also in hot styrene monomer at at least about 150° F.

This equimolar acid addition salt while in chunks did not dissolve in styrene at lower temperatures, and may not also in benzene, toluene, and xylene. However, in much reduced size, for example, as its fine white powder, it dissolves at lower temperatures on stirring in styrene, benzene, toluene, or xylene and within ten minutes at ambient temperature. It is insoluble in hexane, cyclopentane, cyclohexane, and in pentane up to its boiling point. However, it dissolves in pentane to a concentration of about 30 percent at about 120° F. and corresponding superatmospheric pressure to yield a clear and colorless solution, from which upon cooling to about 80° F. the acid addition salt completely precipitates out.

Example 1 can be repeated by replacing its tertiary-butylaminoethyl methacrylate by a gram mole quantity of each of the other secondary-aminoethyl methacrylates with up to about 6 carbons in the sole N-alkyl group, namely, 2-(mono)methylaminoethyl methacrylate, 2-(mono)ethylaminoethyl methacrylate, 2-(mono)propylaminoethyl methacrylate, 2-(mono)isopropylaminoethyl methacrylate, 2-(mono)n-amylaminoethyl methacrylate, 2-(mono)isoamylaminoethyl methacrylate, and 2-(mono)hexylaminoethyl methacrylate respectively.

Thereby there are obtained separately respectively the corresponding equimolar acid addition salts of equimolar amounts of (a) each of these just identified individual secondary-aminoethyl methacrylates and (b) methacrylic acid, and with each having substantially the same properties of the addition salt of Example 1. Each of which additional acid addition salts thus is included herein as if each one of those repeated examples with substitution of the respectively named secondary-aminoethyl methacrylate was set forth in full herein.

In contrast to the tough solid, opaque mass product of Example 1, no solid product at all was obtainable using a tertiary-aminoethyl methacrylate. Thus, just as in Example 1, 86 grams of glacial methacrylic acid and separately 157 grams of 2-(dimethylamino)ethyl methacrylate were poured at the same time into an aluminum pot with vigorous shaking. Directly an exothermic reaction occurred, resulting in a clear amber-like liquid which remained liquid on cooling, and also after extended standing.

EXAMPLE 2

Excess-acid unequal-molar acid addition salts:

a. Three mols percent excess:

92.6 grams (0.5 mole) of 2-(mono)tertiary-butylaminoethyl methacrylate and 44.5 grams (0.515 mole) of glacial methacrylic acid were separately poured with stirring in two separate streams, with less regard to the relative pouring rate of one to one another, into a 250 milliliter beaker. Soon during the mixing, heat evolved. The mixing was continued until the liquid reaction mixture was uniform, and then was discontinued.

On cooling partially, the reaction mixture solidified within a matter of about twenty minutes into a uniformly waxy-appearing solid which was found to be readily frangible because it broke down easily, for example, as by puncturing with a spatula or stirring rod, into smaller and smaller still waxy solid pieces as stirring continued.

b. Five mole percent excess:

Example 2(a) was repeated but instead of its 44.5 grams of the methacrylic acid there was used 45.4 grams (0.525 mole) of it and without any regard to the respective rates of addition of the reactants. The same results with the same type of solid reaction product with its similar frangibility were obtained.

c. Ten mole percent excess acid:

Example 2(b) was repeated but instead of its 45.4 grams of methacrylic acid there was used 47.6 grams (0.55 mole) with the same results and same general properties of end product.

d. Twenty-five mole percent excess acid:

Example 2(b) was repeated but instead of its 45.4 grams of methacrylic acid there was used 54.1 grams (0.625 mole) of it and with the same results and same general properties of end product.

e. Fifty mole percent excess acid:

Example 2(b) was repeated except that instead of 45.4 grams of methacrylic acid there was used 64.9 grams (0.75 mole) and again with the same results and same properties of end product.

EXAMPLE 3

Excess-ester acid addition salts:

i. Three mole percent excess-ester:

43.2 grams (0.5 mole) of methacrylic acid and 95.4 grams (0.515 mole) of 2-(mono)tertiary-butylaminoethyl methacrylate were poured into a 250 ml. beaker in the same way as in Example 2(a) and treated in the same way as in it with the same results and end product of the same general properties.

ii. Five mole percent excess-ester:

Example 3(i) was repeated except that 97.3 grams (0525 mole) of the secondary-aminoethyl ester was used in place of its 95.4 grams and without regard to the respective rates of addition of the reactants. The same results and end product with the same general properties were obtained.

iii. Ten mole percent excess-ester:

Example 3(ii) was repeated except that instead of its 97.3 grams of the ester there were used 101.9 grams (0.55 mole) of it. The same results and end product of the same general properties were obtained.

iv. Twenty-five mole percent excess-ester:

Example 3(ii) was repeated except that instead of its 97.3 grams of the ester there were used 116 grams (0.625 mole) of it, with the same results and solid end product having the same general properties as above described.

v. Fifty mole percent excess-ester:

Example 3(ii) was repeated except that instead of its 97.3 grams of the ester there were used 139 grams (0.75 mole) of it, with the same results and solid end product having the same general properties as above described.

Each of the Examples 2(a) through 2(e) and Examples 3(i) through 3(v) can be repeated by replacing its tertiary-butylaminoethyl methacrylate content by the same respective gram molar quantity of each of the other 2-mono(lower)alkylaminoethyl methacrylates having up to about 6 carbon atoms in its lower-alkyl group, such as those named in the first sentence of the last paragraph of Example 1 above.

Thereby there are provided thus separately respectively (A) the corresponding excess-acid unequal-molar acid addition salts having the respective mol percent excess of glacial methacrylic acid of each of the Examples 2(a) through 2(e), and (B) also the corresponding excess-ester unequal-molar acid addition salts having the same respective mol percent excess of its ester as that of each of Examples 3(i) through 3(v), of each of these other just identified individual secondary-aminoethyl methacrylates; and with each such additional unequal-molar acid addition salt having substantially the same properties as the respective unequal-molar acid addition salt of Examples 2(a) through 3(v).

Each of which said additional excess-acid and excess-ester unequal-molar addition salt thus is included herein as if each one of those repeated examples with the just described substitution of the respectively different secondary-aminoethyl methacrylate was recited in full herein.

An already indicated important use of the unequal-molar acid addition salts as those of the Examples 2(a) through (e) and Examples 3(i) through 3(v) and the just above-described modifications of both sets of them is the improved method of preparing the equimolar acid addition salts by using as starting material an excess-acid unequal-molar acid addition salt together with an excess-ester such addition salt.

One aspect of that method embraces initially preparing from glacial methacrylic acid and the selected 2-mono(lower)alkylaminoethyl methacrylate (a) an excess-acid unequal-molar acid addition salt of at least such molar percent excess of the acid, and also (b) an ester-excess acid addition salt of the same such molar percent excess of ester, which requires at most only little control of the respective rates of feeding the methacrylic acid and the ester; then reducing both of said excess-acid and excess-ester acid addition salts to smaller sizes and admixing them and agitating their mixture until their mixture is converted substantially completely to the equimolar acid addition salt in finely divided particle size.

Thus, in its broadest scope this improved method of making the equimolar acid addition salt comprises (a) mixing (i) the solid excess-acid addition salt of methacrylic acid and a 2-mono(lower)alkylaminoethyl methacrylate whose alkyl group has up to about 6 carbons with a solid excess-ester acid addition salt of methacrylic acid and the same secondary-aminoethyl ester having the same molar percent of excess ester as the molar percent of excess acid in that excess-acid unequal-molar acid addition salt, and (b) agitating their mixture until it is converted substantially completely to the equimolar acid addition salt in finely divided particle size.

This improved method of making the substantially equimolar acid addition salt is illustrated by, but not restricted to, the following:

EXAMPLE 4

The 157.5 grams of the solid 50% excess-acid unequal-molar acid addition salt of Example 2(e) was thoroughly mixed in a 500 ml. beaker with the 182.2 grams of the solid 50 mole percent excess-ester of Example 3(v) with a spatula until no further increase in temperature by the heat of the exothermic reaction was noted and all of the admixed reactants were converted substantially completely to the equimolar acid addition salt in finely divided particle size, which mixing took about 15 minutes.

The equimolar acid addition salt can be prepared by similarly admixing the respective products of Examples 2(d) and 3(iv), or of Examples 2(c) and 3(iii), and likewise also mixing the products of Examples 2(b) and 3(ii), as well as also similarly admixing the products of Example 2(a) and Example 3(i), in each case until the total of both of the respective excess-acid and excess-ester unequal acid addition salts was converted substantially completely to the equimolar acid addition salt in finely divided particle size.

The corresponding equimolar acid addition salt of methacrylic acid and any other 2-mono(lower)alkylaminoethyl methacrylate whose alkyl has up to about 6 carbons can be prepared similarly by repeating in the same way any of the above described separate embodiments of Example 4, but replacing its two starting excess-acid and excess-ester unequal-molar acid addition salts respectively by the two other such unequal-molar acid addition salts, in each of which the ester component is the desired other applicable monoalkylaminoethyl methacrylate.

These unequal acid addition salts manifest certain anti-corrosion activity. For example, on dissolving methacrylic acid in water having steel wool immersed in it, the characteristic bubbling occurs at the steel wool surfaces from the hydrogen evolution following attack on the steel wool by that acid. However, no bubbling occurs when steel wool is immersed (and even agitated) in water when either the excess acid or the excess-ester unequal acid addition salt of this invention is dissolved in the water.

Also, when 1 gram of steel wool was immersed in 50 ml. of water, rust developed in 4 hours. Then too, when 1 gram of steel wool was immersed in 50 ml. of water containing dissolved separately 0.5 gram of glacial methacrylic of acid or mono-(tertiary)butylaminoethyl methacrylate the solution turned light tan within 12 hours. However, when the water contained dissolved in it instead 0.5 gram of either the 50% excess-acid or excess-ester acid addition salt of Examples 2(e) or 3(v) respectively separately, the solution was still clear even beyond at least 24 hours so far as presently tested. Then too, there was no evolution of gas from the immersion of the steel wool in the solution of the excess-acid acid addition salt.

The advantageous feature of the invention stemming from the unobvious property of the equimolar acid addition salt of the invention to provide the possibility of solution co-polymerization of some polymerizable monomers, such as styrene and acrylonitrile, which when sought to be copolymerized in solution otherwise are prone to yield undesirably low viscosity polymer solutions giving weak and brittle films cast therefrom, is illustrated by, but not restricted to, the following examples:

EXAMPLE 5

Solution co-polymerization of styrene and acrylonitrile with equimolar acid addition salt:

120 ml. of styrene, 28 ml. of acrylonitrile, 200 ml, of methyl ethyl ketone, 180 ml. of xylene, 3 ml. of tricresyl phosphate, and 3 ml. of butyl benzyl phthallate were mixed in a liter beaker, and into their mixture 0.6 gram of alpha, alpha'-azo-bis-isobutyronitrile and 0.02 gram of benzoyl peroxide were uniformly admixed.

Seven grams of the finely divided equimolar acid addition salt of Example 1 were placed in a stainless steel pressure reactor, to which was added 225 ml. of the just described solution of the monomers styrene and acrylonitrile in the solvents methyl ethyl ketone and xylene, with the included phosphate and phthallate plasticizers and the nitrile and peroxide catalyst.

The reactor was sealed with its cap screwed pressure-tightly over the outside threads of its neck with a teflon-tape seal between the cap and the threads. The reactor was rotated about its own axis in a water bath maintained at 160° F., for 16 hours to obtain substantially complete conversion.

The resulting styrene-acrylonitrile copolymer solution in the methyl ethyl ketone and xylene is a transparently clear coating lacquer. Application of single coatings of this lacquer over metal surfaces, especially nonferrous metals as copper, brass, bronze, as well as over iron, steel and ferrous metal surfaces, after evaporation of the solvents and without subsequent baking, left them with a strongly adhesive clear transparent continuous thin film which protected and preserved their bright clean original surfaces from atmospheric change for long extended periods, such as even a couple of years or more as with the copper.

Other variations and applications of the coating lacquer of this example occur further below.

While the styrene and acrylonitrile are used in the foregoing example in the ratio of about 5 parts of styrene to one of acrylonitrile, their ratios can be varied. For example, the acrylonitrile may be reduced possibly to even half of its proportion. Alternatively, the acrylonitrile may be increased toward equal to the styrene and also can exceed it even to about five times the styrene. However, as the acrylonitrile ratio is increased up to about equal the styrene, to avoid turbidity or other evidence of inadequate acrylonitrile solution the xylene ought to be replaced, initially at least in part and otherwise as a whole, by dimethylformamide and/or dimethyl sulfoxide.

It is advantageous generally to retain the azo-bis-diisobutyronitrile catalyst. However, the benzoyl peroxide catalyst may be entirely omitted or replaced in part or as a whole by cumene hydroperoxide and/or tertiary-butyl hydroperoxide or di-(tertiary)butyl hydroperoxide, or any other free-radical type catalyst suitable to the polymerization conditions used.

While for certain applications of a coating lacquer formulation like that of Example 5, such as the above-mentioned protective coating of metal surfaces, the plasticizer may be omitted, in other applications only tricresyl phosphate was used in a proportion equal to that of both of the plasticizers in that formulation. However, in working with this modification for some other uses, the tricresyl phosphate indicated tendency of bleeding or migration. This there undesirable tendency was avoided when the tricresyl phosphate was replaced up to, say, about 50% by a plasticizer such as butyl benzyl phthallate or dioctyl phthallate and the like. Their joint use was found to provide a more stable and higher gloss to the finished film than that obtained with tricresyl phosphate alone.

The methyl ethyl ketone could be used alone without xylol, but the latter and/or toluene reduces the cost by up to possibly as much as 60%. That ketone also could be replaced in part or as a whole by any other suitable ketone solvent such as methyl isobutyl ketone, diethyl ketone, diisobutyl ketone, ethyl butyl ketone, methyl n-amyl ketone, methyl isoamyl ketone, or methyl propyl ketone, depending on the various drying conditions. Such other variations in the Example 5 formulation provide other transparent coating lacquers with corresponding variations in properties.

A further variation of the provision of the possibility of doing solution co-polymerization of styrene and acrylonitrile and including another polymerizable substance is shown by, but not restricted to, the following illustrative also of a pigmented coating:

EXAMPLE 6

Pigmented coating based on styrene, acrylonitrile, styrene-butadiene, and equimolar acid addition salt:

8 pounds of the equimolar acid addition salt of Example 1, 72 lbs. of styrene, 16 lbs. of acrylonitrile, 30 lbs. of 10% GRS 1006 rubber solution, 16 lbs. of tetrahydrofuran, 9 gallons of xylene, 8 gallons of methyl ethyl ketone, 13 lbs. of 4-methoxy-4-methyl-pentanone-2, 13 lbs. of 'Cyclosol No. 53' (Shell Chemical Company's mixed solvent aromatics), 6 lbs. of mineral oil (medium) USP, 6 lbs. tricresyl phosphate, 6 lbs. butyl benzyl phthallate, 80 lbs. titanium dioxide (pigment RA51, Titanium Corp. of America), 10 lbs. 'Opti-White' (Burgess Pigment Corp'n, Sandersville, Ga.) anhydrous aluminum silicate, 180 grams azo-bis-isobutyronitrile, 4.5 grams benzoyl peroxide, 4.5 grams di-(tertiary)butyl catechol, 4.5 grams of trinonyl phosphite, 360 grams of lecithin (syrup), and 110 lbs. of flintstone grinding pebbles are loaded into a cylindrical pressure reactor having a bolted on cap on each end, with its longitudinal axis being about three times its diameter.

This reactor is removably mounted for rotation about an axis diametrically normal to the middle of its longitudinal axis, and rotatably supported by its rotation shaft extending diametrically oppositely outwardly from the cylinder wall of the reactor and along its axis of rotation. As so mounted and submerged in a water tank maintained at a polymerization temperature of 174° F. (± 2.5° F.), the reactor is rotated slowly (e.g. 3 rpm) for a time sufficient for the conversion to be completed — 18 hours.

The rotation then is interrupted and there is added 3 gallons of an epoxy resin solution composed of 32 lbs. of 'Epon 1001' and 4 lbs. of 'Epon 828' (both epoxy resins of Shell Chemical Co., New York, N.Y.), 70 lbs. each of xylene and tetrahydrofuran and a half gallon dimethylformamide, and resumed for long enough (25 minutes or so) to affect their uniform admixture.

The product as thus completed is effective as an advantageous quick-drying final coating for various applications to provide high highing power, flexibility, strong adhesion and abrasion resistance, with extensive corrosion and weather resistance. For other applications it is diluted with compatible solvents, such as equal parts (by weight) of xylene and methyl ethyl ketone, to provide the specifically suitable viscosity for the use, for example, 20 seconds Zahn cup.

These pigmented co-polymerized styrene-acrylonitrile coatings are not to be restricted to the exact formulation of Example 6. Variations in its monomers, solvents, catalyst, plasticizer, antioxidant, and diluents can be made as described in relation to Example 5. Other compatibly suitable white or other color pigments, e.g. aluminum and/or zinc powders, or the wide range of the different iron oxide pigments can replace the titanium dioxide in part or as a whole.

The lecithin provided a significant and stable plasticizing effect on these pigment-bearing polymers prepared with styrene in addition to enhancing wetting of the pigment by the organic polymer and solvent system and providing improved pigment dispersion and stability of particle distribution.

Polymerization of these acid addition salts of the invention is shown, for example, by that of the equimolar acid addition salts as illustrated by, but not restricted to, the following polymerization and resulting product:

EXAMPLE 7

Polymerization product of equimolar acid addition salt:

Thirty-six grams of the equimolar acid addition salt of methacrylic acid and 2-(mono-tertiary-butylamino)ethyl methacrylate of Example 1, and 115 grams of pentane, together with 0.2 grams of the alpha, alpha' azo-bis-isobutyronitrile as catalyst were loaded into a seven ounce heavy-walled, narrow-necked glass pressure-bottle and pressure-tightly sealed therein by an aluminum inner-lined cork insert metal cap mechanically secured by pressure crimping to the bottle neck.

The sealed polymerization pressure-bottle was mounted for rotation at 40 r.p.m. about an axis normal to its longitudinal axis and intermediate its ends in a temperature-controlled water-bath. When the bath temperature reached 130° F., the acid addition salt was noted to have dissolved in the pentane. The heating was continued until the bath reached 150° F. and the rotation continued with the bath maintained at it when the polymerization was complete at the end of a 24 hour cycle at 150° F.

This equimolar acid addition salt polymer formed as a very finely divided white solid suspension in the pentane, in which it was insoluble. This polymer was filtered off easily from the pentane and dried readily at room temperature and pressure as the entrained pentane evaporated off, leaving behind the extremely fine polymeric product. This product was so fine that it floated upwardly out of a jar in which it was kept, upon removing the cover of the jar.

This white powder resisted fusion at observed temperatures up to 600° F. At about 700° F. it discolored and softened, and exposed to the air at that level after 5 minutes it turned brown and assumed a rubbery character.

This finely divided equimolar acid addition salt polymer dissolved in water readily at all concentrations up to 50 percent (the highest tried). Evaporation of the water from a coating of its aqueous solution on paper, glass, and other surfaces left a water-white, tough and flexible film. The 50% aqueous solution was clear and quite viscous.

The polyamphoteric character of this equimolar acid solution salt polymer is shown by the typical dual peaks (one on the acid side and the other on the alkaline) separated by the trough between them — on plotting its viscosity versus pH.

This polyamphoteric equimolar acid addition salt polymer also manifests sequestration effectiveness. For example, immersion of 0.5 gram of steel wool in a 1% aqueous solution of the polymer withstood precipitation of any iron oxide at from ambient temperature even to heating at 150°F. for a couple of hours and then showed only a yellowish to amber clear solution. On the other hand, the control sample (without any dissolved polymer) showed a brownish precipitate within 2 hours at 150° F.

Addition of sodium hydroxide to pH 11 produced no precipitate in the aqueous sample containing 1% of the equimolar acid addition salt polymer with the immersed steel wool. Addition of hydrochloric acid to give pH 2 to 100 ml. of the 1% aqueous solution of the polymer with 0.5 gram of steel wool immersed in it after 10 days showed only a slight yellowish discoloration and no precipitate. In the control sample which contained no polymerized equimolar acid addition salt, the steel wool was completely dissolved in 4 days.

A jar of sea water with a steel nail immersed in it showed a brownish precipitate of iron oxide within 4 hours. Yet a similar jar with 1% of this polymerized acid addition salt dissolved in the sea water remained stable without change over a test period extended to 3 months.

This polymerized acid addition salt also shows utility to enhance the effectiveness of dissolved ferric ion in the redox formulation for emulsion polymerization, as with styrene; as illustrated by, but not restricted to, the following:

EXAMPLE 8

Comparison in emulsion polymerization:

A. 120 ml. of commerical spring water, 1.5 grams of the polymerized equimolar acid addition salt of Example 7 (briefly called Example 7 polyampholyte), 0.4 gram each of ammonium persulfate and of sodium metabisulfite, 2 grams of ferrous sulfate solution (of 0.3 gram ferrous sulfate per 100 ml. water), and 60 grams of styrene (monomer) were loaded into an 8 ounce pressure bottle like the one described in Example 7.

B. Another such bottle was prepared with the same content except that 0.5 gram of its Example 7 polyampholyte was replaced by 0.5 gram of a commercial soap (Procter & Gamble's 'Ivory Snow' product).

C. A third such bottle was prepared with the entire 1.5 grams of the polyampholyte of part (A) replaced by 1.5 grams of that 'Ivory Snow' commercial soap.

All of the three bottles were mounted just as was the pressure-bottle of Example 7 and rotated at the same time in the water-bath maintained at 120° F. for 3 hours. These bottles then were allowed to cool, and the respective following percentages of conversion of the styrene were determined:

| A. | Polyampholyte | 1.5 gm. | 100 %; |
|----|---------------|---------|--------|
| B. | Polyampholyte | 1. gm.  |        |
|    |               |         | 55.4%; and |
|    | 'Ivory Snow'  | 0.5 gm. |        |
| C. | 'Ivory Snow'  | 1.5 gm. | 48 %.  |

These results show that the Example 7 polyampholyte so enhanced the emulsion polymerization of styrene that it provided complete conversion in the period in which the other two emulsification agents allowed only 55.4% and 48% conversion respectively.

While the invention has been explained with reference to certain specific embodiments of it, it is understood that various substitutions and modifications can be made in the described embodiments within the scope of the appended claims which are intended also to cover equivalents of these embodiments.

What is claimed is:

1. A solid, water-soluble polymerizable methacrylic acid addition salt of a 2-mono(lower)alkylaminoethyl methacrylate wherein (a) alkyl has up to about 6 carbon atoms and (b) the methacrylic acid and the 2-mono(lower)alkylaminoethyl methacrylate components are present in said salt in the ratio of from one to about 1.5 moles of one per mole of the other.

2. A methacrylic acid addition salt as claimed in claim 1, wherein said methacrylic acid and methacrylate components are present in said salt in equimolar ratio and said addition salt is an equimolar acid addition salt.

3. The acid addition salt as claimed in claim 2, wherein said methacrylic acid component is glacial methacrylic acid.

4. The acid addition salt as claimed in claim 3, wherein said methacrylate component is a 2-(monobutylamino)ethyl methacrylate, said product being opaque, tough yet frangible, soluble in methanol, acetone, methyl ethyl ketone, said styrene, and insoluble in pentane, hexane, cyclopentane, and cyclohexane.

5. The acid addition salt as claimed in claim 4, wherein said methacrylate component is 2-(mono-tertiary-butylamino)ethyl methacrylate.

6. The acid addition salt as claimed in claim 1, wherein the methacrylic acid component and the alkylaminoethyl methacrylate component are present in it in unequal-molar ratio to one another, whereby said solid addition salt is an unequal-molar acid addition salt.

7. The acid addition salt as claimed in claim 6, wherein said methacrylate component exceeds the methacrylic acid component and said solid addition salt thereby is an excess-ester unequal-molar acid addition salt.

8. The excess-ester unequal-molar acid addition salt as claimed in claim 7, wherein said methacrylate component is a 2-(mono-butylamino)ethyl methacrylate.

9. The excess-ester unequal-molar acid addition salt as claimed in claim 8, wherein said butylaminoethyl methacrylate component is 2-(mono-tertiary-butylamino)ethyl methacrylate and said salt is waxy appearing.

10. The acid addition salt as claimed in claim 6, wherein said methacrylic acid and methacrylate components are present in said salt in unequal molar-ratio with said methacrylic acid component exceeding the methacrylate component, whereby said solid addition salt is an excess-acid unequal-molar acid addition salt.

11. The excess-acid unequal-molar acid addition salt as claimed in claim 10, wherein said methacrylate component is a 2-(mono-butylamino)ethyl methacrylate.

12. The excess-acid unequal-molar acid addition salt as claimed in claim 11, wherein said butylaminoethyl methacrylate component is 2-(mono-tertiary-butylamino)ethyl methacrylate.

13. The method of preparing an equimolar acid addition salt as claimed in claim 3, wherein (i) a solid excess-acid unequal-molar acid addition salt having at least about 5 mole percent excess of its methacrylic acid component and (ii) a solid excess-ester unequal-molar acid addition salt having the same mole percent excess of its alkylaminoethyl methacrylate component as the mole percent excess of methacrylic acid in said excess-acid unequalmolar acid addition salt, are admixed and agitated to reduce their original starting size, and the agitation of their admixture is continued until their mixture, heated by the released heat of reaction, is converted by the agitation substantially completely to the equimolar acid addition salt in free-running finely divided particle size.

14. The method as claimed in claim 13, wherein said alkylaminoethyl methacrylate is a 2-(mono-butylamino)ethyl methacrylate.

15. The method as claimed in claim 14, wherein said butylaminoethyl methacrylate is 2-(mono-tertiary-butylamino)ethyl methacrylate.

* * * * *